(12) United States Patent
Schreder et al.

(10) Patent No.: US 6,491,946 B1
(45) Date of Patent: Dec. 10, 2002

(54) PHARMACEUTICAL LEVOTHYROXINE PREPARATION

(75) Inventors: Sven Schreder, Heidelberg (DE); Marion Nischwitz, Darmstadt (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/743,114

(22) PCT Filed: Jun. 29, 1999

(86) PCT No.: PCT/EP99/04485
§ 371 (c)(1),
(2), (4) Date: Jan. 5, 2001

(87) PCT Pub. No.: WO00/02586
PCT Pub. Date: Jan. 20, 2000

(30) Foreign Application Priority Data

Jul. 7, 1998 (DE) .......................... 198 30 246

(51) Int. Cl.$^7$ .............. A61K 9/14; A61K 9/20
(52) U.S. Cl. ............ 424/465; 424/464; 424/489; 514/774; 514/781; 514/970; 514/961; 514/951
(58) Field of Search ............... 424/464, 465, 424/489

(56) References Cited

U.S. PATENT DOCUMENTS

| 5,225,204 A | 7/1993 | Papademitriou et al. .... 424/484 |
| 5,635,209 A | 6/1997 | Groenwoud et al. ........ 424/464 |

FOREIGN PATENT DOCUMENTS

WO      9717951      5/1997

*Primary Examiner*—James M. Spear
(74) *Attorney, Agent, or Firm*—Millen, White, Zelano & Branigan, P.C.

(57) ABSTRACT

The invention relates to a pharmaceutical preparation comprising levothyroxine sodium, potassium iodide, microcrystalline cellulose and binding agent, which is free of antioxidants or further auxiliaries, and processes for its production.

6 Claims, No Drawings

PHARMACEUTICAL LEVOTHYROXINE PREPARATION

This application is a 371 of PCT/EP99/04485 filed Jun. 29, 1999.

The invention relates to a novel stable pharmaceutical preparation comprising levothyroxine sodium, potassium iodide, microcrystalline cellulose and binding agent, which is free of antioxidants or further auxiliaries.

Auxiliaries are substances which prevent formation of iodine, e.g. potassium hydroxide.

A thyroxine preparation stabilized with thiosulfate as an antioxidant is described in DE 195 41 128.

Another known thyroxine-containing commercial preparation Thyreocomb® N (Red List 1998, 74015) contains the auxiliary potassium hydroxide, which drives the comproportionation reaction of iodide and iodate to iodine to the starting material side. In this manner, production of iodine is suppressed.

A preparation comprising levothyroxine sodium and potassium iodide for the stabilization of the active compound levothyroxine sodium is disclosed in U.S. Pat. No. 5,635,209. For a low dose, the amount of potassium iodide needed for the stabilization of levothyroxine sodium is given in a ratio of 4:1, e.g. 25 $\mu$g of levothyroxine sodium and 100 $\mu$g of potassium iodide. For high doses, the ratio is described as 1.5:1, e.g. 300–450 $\mu$g of potassium iodide for 300 $\mu$g of levothyroxine sodium. 300 $\mu$g of potassium iodide were needed for the stabilization of 100 $\mu$g of levothyroxine sodium.

The active compound levothyroxine sodium (=levothyroxine-Na=LT4) is sensitive to light, heat and oxygen. On account of these known stability problems, pharmaceutical preparations are therefore overdosed by up to 20%.

If, in addition to the active compound levothyroxine-Na in a pharmaceutical preparation, iodide is additionally contained, this pharmaceutical preparation becomes discoloured on storage, since the anion iodide in potassium iodide can be oxidized to iodine or can comproportionate with potassium iodate to give iodine. Furthermore, the demands on the in-vitro release for levothyroxine-Na tablets have been increased. The draft monograph of the Pharmacopeial Forum (Pharm. Preview, 1995, 21, 1459–1461) intends, in addition to the valid test 1 (phosphate buffer pH 7.4, in 80 minutes >55%), to approve the test 2 (water in 45 minutes >70%).

The invention was based on the object of making available novel medicaments in the form of pharmaceutical preparations which have better properties than known medicaments which can be used for the same purposes.

This object was achieved by the discovery of the novel preparation.

The novel preparation according to the invention essentially shows no discolouration and has an improved stability. It can be used as a thyroid hormone combination preparation, owing to the high content of iodide as a second active compound, in euthyroid iodine deficiency goitre and/or in relapse prophylaxis after resection of an iodine deficiency goitre.

The active compound iodide can be contained as an anion only in the presence of a stabilizing cation, e.g. potassium ($^+$), and thus as a salt in a pharmaceutical preparation. 130 $\mu$g of potassium iodide correspond to 100 $\mu$g of iodide.

Discolouration of the preparation according to the invention is avoided, since formation of free iodine is prevented.

This novel preparation furthermore has a very good release of active compound in vitro.

The invention preferably relates to a pharmaceutical preparation as described, characterized in that it contain 5 to 400 $\mu$g, of levothyroxine 300 $\mu$g, in particular 50 to 200 $\mu$g, of levothyroxine sodium and 5 to 400 $\mu$g, preferably 10 to 300 $\mu$g, in particular 25 to 200 $\mu$g, of potassium iodide.

The invention furthermore preferably relates to a pharmaceutical preparation as described, characterized in that it contains levothyroxine sodium in micronized form having a particle size of between 5 and 25 $\mu$m (to 95%), particularly preferably having a particle size of between 5 and 15 $\mu$m (to 95%).

The invention furthermore preferably relates to a pharmaceutical preparation as described, characterized in that it contains a hydroxypropyl-methylcellulose and/or gelatine as a binding agent.

A pharmaceutical preparation is particularly preferably described, characterized in that it is a solid preparation in the form of tablets.

Particularly preferred embodiments contain 50, 75 or 100 $\mu$g of levothyroxine sodium and 100 $\mu$g each of iodide, 100 $\mu$g of iodide corresponding to an amount of 130 $\mu$g of potassium iodide. A very particularly preferred embodiment contains 100 $\mu$g of levothyroxine sodium and 100 $\mu$g of iodide.

On account of the known instability of levothyroxine-Na, this active compound is overdosed to 5% in the formulations.

The preparation according to the invention has a surprising stability when hydroxypropylmethyl-cellulose and/or gelatine is used as a binding agent. At the same time, formation of iodine is surprisingly suppressed without admixture of antioxidants or further auxiliaries being necessary.

The data of the stability investigations are indicated in Tables I and II as exemplified by batches 005204 (13/97) and 004609 (3/96). Based on the results, it can be seen that the tablets according to the invention which contain levothyroxine sodium (100 $\mu$g) and iodide (100 $\mu$g) are stable for at least 2 years if they are stored at temperatures below 30° C. Likewise, no brown colouration of the pharmaceutical preparation is observed in this period, i.e. no formation of iodine.

Furthermore, the release of the active compound levothyroxine sodium is favoured if the active compound is employed in micronized form. Levothyroxine sodium is customarily soluble with great difficulty both in water and in ethanol. With a particle size of between 5 and 25 $\mu$m (to 95%), particularly preferably between 5 and 15 $\mu$m, however, a release of the active compound which corresponds to both test systems takes place (Tables I and II).

TABLE I

Stability and release of batch 005204 (13/97); levothyroxine-Na (LT4) 100 μg/iodide 100 μg tablets; prepared analogously to Example 1:

PP tube 25°/60%

| Period<br>Date (storage)<br>Date (investigation) | Content<br>of LT4<br>[μg] | Content<br>of iodide<br>[μg] | Release<br>with<br>buffer<br>[%] | Release<br>with<br>water<br>[%] | Water content<br>according<br>to KF<br>[%] | Disintegration<br>time<br>[sec] | Friability<br>[N] |
|---|---|---|---|---|---|---|---|
| Starting value | 108.3 | 99.5 | 30 min: 94.3<br>60 min: 99.2<br>80 min. 100.6 | 15 min: 91.3<br>30 min: 93.5<br>45 min: 95.1 | 2.51 | 43–55 | 42–50 |
| 13 weeks<br>18.07.1997<br>13.02.1998 | 106.9 | 104.2 | | 15 min: 85.9<br>30 min: 89.9<br>45 min: 91.2 | 3.28 | 50–60 | 48–55 |
| 26 weeks<br>17.10.1997<br>21.02.1998 | 102.1 | 102.8 | | 15 min: 89.5<br>30 min: 91.6<br>45 min: 95.1 | 3.14 | 50–68 | 41–48 |
| 39 weeks<br>19.01.1998 | 100.6 | 103.2 | | 15 min: 84.6<br>30 min: 88.1<br>45 min: 89.3 | 3.28 | 49–60 | 41–49 |
| 52 weeks | 100.9 | 103.2 | | 15 min: 84.6<br>30 min: 87.2<br>45 min: 89.5 | 3.50 | 40–55 | 41–49 |

Comments: 5% overdosage of LT4

TABLE II

Stability and release of batch 004609 (3/96); levothyroxine-Na (LT4) 100 μg/iodide 100 μg tablets; prepared analogously to Example 1:

PP blister 25°/60%

| Period<br>Date (storage)<br>Date (investigation) | Content<br>of LT4<br>[μg] | Content<br>of iodide<br>[μg] | Release<br>with<br>buffer<br>[%] | Release<br>with<br>water<br>[%] | Water content<br>according<br>to KF<br>[%] | Disintegration<br>time<br>[sec] | Friability<br>[N] |
|---|---|---|---|---|---|---|---|
| Starting value | 108.3 | 103.6 | 30 min: 105.3<br>60 min: 105.3<br>80 min: 103.1 | 15 min: 101.0<br>30 min: 102.9<br>45 min: 106.1 | 3.18 | | |
| 13 weeks<br>23.12.1996 | 104.9 | 100.2 | 15 min: 94.6<br>30 min: 96.3<br>45 min: 96.7 | | 4.8 | | |
| 26 weeks<br>10.04.1997<br>24.02.1998 | 104.8 | 103.6 | 15 min: 96.1<br>30 min: 97.2<br>45 min: 97.4 | | 5.34 | | |
| 52 weeks<br>29.09.1997 | 101.5 | 102.7 | | 15 min: 94.1<br>30 min: 95.3<br>45 min: 95.8 | 6.26 | 37–50 | 39–44 |
| 78 weeks<br>24.02.1998 | 99.72 | 104.6 | | 15 min: 95.8<br>30 min: 97.5<br>45 min: 98.6 | 5.69 | 30–38 | 35–40 |

Comments: 5% overdosage of LT4

The analytical data are determined according to customary and known methods.

The invention also relates to a process for the production of a pharmaceutical preparation comprising levothyroxine sodium and potassium iodide, characterized in that levothyroxine sodium and potassium iodide, which are present in suspended form in aqueous hydroxypropylmethylcellulose and/or gelatine solution, are sprayed onto the microcrystalline cellulose in a fluidized bed granulation, then a disintegrating agent and lubricant are admixed and the mixture is compressed to give tablets.

Hydroxypropylmethylcellulose and potassium iodide are dissolved in water and levothyroxine sodium is suspended in water at temperatures between 5 and 40° C., preferably between 10 and 35° C., particularly preferably between 15 and 30° C.

The temperature during the granulation is between 60 and 80° C., preferably between 65 and 75° C., at the inlet and between 10 and 50° C., preferably between 20 and 40° C., at the outlet. The spray pressure in the process according to the invention is between 3 and 5 bar.

The invention further relates to a process as described, characterized in that the disintegrating agent used is croscarmellose sodium and the lubricant used is magnesium stearate.

Further excipients or additives can be added, such as, for example, binding agents, colourants, lubricants, sweeteners and/or aromatic substances.

Preferred glidants or lubricants are, for example, talc, starch, magnesium stearate and calcium stearate, boric acid, paraffin, cocoa butter, macrogol, leucine or sodium benzoate; magnesium stearate is very particularly preferred.

The preparation according to the invention can be prepared without the use of organic solvents.

The following examples relate to the production and the composition of the pharmaceutical preparation according to the invention:

EXAMPLE 1

The following amounts are needed in order to prepare, for example, 50,000 tablets:

Levothyroxine 100 µg/iodide 100 µg

| Ingredient | Amount [g] |
|---|---|
| Levothyroxine sodium* | 5.25 |
| Potassium iodide | 6.54 |
| Hydroxypropylmethylcellulose | 175.00 |
| Microcrystalline cellulose | 4125.70 |
| Croscarmellose sodium | 175.00 |
| Magnesium stearate | 12.50 |
| Water, purified** | 3259.00 |

*A 5% overdosage for levothyroxine sodium was additionally included.
**The water is removed again by drying.

Production

1. Hydroxypropylmethylcellulose and potassium iodide are dissolved in about 90% of the water at room temperature with stirring.

Levothyroxine sodium is suspended in about 10% of the water at room temperature.

The suspension is then combined with the hydroxypropylmethylcellulose/potassium iodide solution with the aid of a mixer.

2. The microcrystalline cellulose is introduced into a fluidized bed granulator. The granulating liquid is sprayed over the powder. During the granulation, the temperature is kept at approximately 7° C. (+5° C.) at the inlet and between 20 and 40° C. at the outlet. The spray pressure is between 3 and 5 bar.

After spraying, the granules are dried until a temperature of approximately 40° C. is reached at the outlet.

The dry granules are then sieved (1 mm) according to known methods (=mixture a).

Croscarmellose sodium and magnesium stearate are correspondingly sieved. The components are then mixed with one another for 10 minutes in a drum mixer together with mixture a.

The ready-to-press mixture is then compressed to give tablets.

EXAMPLE 2

Composition of a 90 mg (±3 mg) tablet which contains 105 µg of levothyroxine sodium and 130 µg of potassium iodide and thus 100 µg of iodide:

| | |
|---|---|
| levothyroxine sodium | 0.105 mg |
| potassium iodide | 0.1308 mg |
| water* | 65.00 mg |
| hydroxypropylmethylcellulose | 3.50 mg |
| cellulose, microcrystalline | 82.514 mg |

-continued

| | |
|---|---|
| croscarmellose sodium | 3.50 mg |
| magnesium stearate | 0.25 mg |
| | 90.00 mg |

Levothyroxine sodium is overdosed by 5%.
*water is removed by drying.

Comparison Example

The following amounts are needed in order to prepare, for example, 60,000 tablets:

Levothyroxine 100 µg/KI 300 µg

| Ingredient | Amount [g] |
|---|---|
| Levothyroxine sodium* | 7.03 |
| Potassium iodide | 17.99 |
| Cellulose | 5885.72 |
| Croscarmellose sodium | 50.00 |
| Magnesium stearate | 25.00 |
| Water, purified** | 4140.00 |

*A 5% overdosage for levothyroxine sodium was included.
**The water is removed again by drying.

Preparation

1. Levothyroxine sodium (1.05%) and about 10% of the cellulose are sieved and mixed for 20 minutes in a Turbula mixer.
2. The potassium iodide (18%) is dissolved in 60% of the water. 54% of the cellulose is moistened with this solution and the treated cellulose is kneaded and sieved (1 mm). After drying in vacuo at room temperature, the resulting granules (0.1% of KI) are sieved through a 0.75 mm sieve.
3. The remaining amount of potassium iodide (82%) is applied to cellulose in the third stage analogously to stage 2. Sieved granules comprising 0.7% of KI are obtained.
4. Sodium carboxymethylcellulose (Croscarmellose sodium) and magnesium stearate are correspondingly sieved (0.5 mm).
5. The granules or solid mixtures obtained from stages 1 to 4 are combined and mixed according to known methods for 20 minutes. Tabletting is carried out in a rotary press (13 kN press force).

The tablets are yellow- to brown-coloured.

What is claimed is:

1. A pharmaceutical composition comprising levothyroxine sodium, potassium iodide, microcrystalline cellulose and hydroxypropylmethylcellulose or gelatine or both hydroxypropylmethylcellulose and gelatine, which is essentially free of antioxidants.

2. A pharmaceutical composition according to claim 1 comprising 5 to 400 µg of levothyroxine sodium and 5 to 400 µg of potassium iodide.

3. A pharmaceutical composition according to claim 1 wherein the levothyroxine sodium is in micronized form having a particle size of 5 to 25 µm.

4. A pharmaceutical composition according to claim 1, wherein the composition is solid in the form of tablets.

5. A process for the preparation of a pharmaceutical composition comprising levothyroxine sodium, potassium iodide, microcrystalline cellulose and a binding agent, which is essentially free of antioxidants, said process comprising spraying an aqueous hydroxypropylmethylcellulose and/or gelatine solution comprising levothyroxine sodium and potassium iodide which are present in suspended form in said solution onto microcrystalline cellulose in a fluidized bed granulation, admixing a disintegrating agent and a lubricant and compressing the resultant mixture to form tablets.

6. A process according to claim 5, wherein the disintegrating agent is croscarmellose sodium and the lubricant is magnesium stearate.

* * * * *